United States Patent
Kominami et al.

(10) Patent No.: US 11,202,764 B2
(45) Date of Patent: Dec. 21, 2021

(54) PATCH

(71) Applicant: HISAMITSU PHARMACEUTICAL CO., INC., Tosu (JP)

(72) Inventors: Kazuya Kominami, Tsukuba (JP); Takito Shima, Tsukuba (JP); Naoyuki Uchida, Tsukuba (JP); Naoko Fujita, Tsukuba (JP); Shigeo Suzuki, Tokyo (JP); Terumitsu Kaiho, Tokyo (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 164 days.

(21) Appl. No.: 16/605,268

(22) PCT Filed: Apr. 19, 2018

(86) PCT No.: PCT/JP2018/016115
§ 371 (c)(1),
(2) Date: Oct. 15, 2019

(87) PCT Pub. No.: WO2018/198924
PCT Pub. Date: Nov. 1, 2018

(65) Prior Publication Data
US 2020/0121613 A1  Apr. 23, 2020

(30) Foreign Application Priority Data

Apr. 25, 2017 (JP) .............................. JP2017-086357
Jun. 30, 2017 (JP) .............................. JP2017-129601

(51) Int. Cl.
*A61K 9/70* (2006.01)
*A61K 47/12* (2006.01)
*A61P 25/04* (2006.01)
*A61K 31/485* (2006.01)

(52) U.S. Cl.
CPC .......... *A61K 9/7069* (2013.01); *A61K 9/7061* (2013.01); *A61K 31/485* (2013.01); *A61K 47/12* (2013.01)

(58) Field of Classification Search
CPC ...... A61K 31/485; A61K 47/12; A61K 47/32; A61K 47/34; A61K 9/7061; A61K 9/7069; A61P 25/04
See application file for complete search history.

(56) References Cited

U.S. PATENT DOCUMENTS

| | | | |
|---|---|---|---|
| 3,775,414 A | 11/1973 | Monkovic et al. | |
| 4,626,539 A | 12/1986 | Aungst et al. | |
| 10,888,532 B2 * | 1/2021 | Fujita | A61K 47/10 |
| 2005/0042271 A1 * | 2/2005 | Xiong | A61K 9/7061 |
| | | | 424/449 |
| 2005/0266063 A1 | 12/2005 | Yasukochi et al. | |
| 2006/0078600 A1 | 4/2006 | Muller | |
| 2006/0078603 A1 | 4/2006 | Nguyen | |
| 2006/0110434 A1 * | 5/2006 | Yamaguchi | A61K 9/7053 |
| | | | 424/448 |
| 2008/0226697 A1 | 9/2008 | Yamaguchi et al. | |
| 2009/0246265 A1 | 10/2009 | Stinchcomb et al. | |
| 2011/0091511 A1 | 4/2011 | Nguyen | |
| 2012/0315318 A1 * | 12/2012 | Toshimitsu | A61K 9/7061 |
| | | | 424/443 |
| 2014/0161865 A1 | 6/2014 | Higo et al. | |
| 2015/0004215 A1 | 1/2015 | Yoshizaki et al. | |
| 2017/0224630 A1 | 8/2017 | Noguchi et al. | |

FOREIGN PATENT DOCUMENTS

| | | | | |
|---|---|---|---|---|
| CA | 2962080 A1 * | 3/2016 | .......... | A61K 31/485 |
| EP | 1 611 882 A1 | 1/2006 | | |
| EP | 2 740 472 A1 | 6/2014 | | |
| EP | 2 818 161 A1 | 12/2014 | | |
| JP | 61-083116 A | 4/1986 | | |
| JP | 07-053357 A | 2/1995 | | |
| JP | 2006-001859 A | 1/2006 | | |
| JP | 2006-045099 A | 2/2006 | | |
| TW | 200616589 A | 6/2006 | | |
| WO | 2005/102393 A1 | 11/2005 | | |
| WO | 2016/060122 A1 | 4/2016 | | |

OTHER PUBLICATIONS

Colon [online] retrieved on May 25, 2021 from: https://www.thepunctuationguide.com/colon.html; 1 page. (Year: 2021).*
Office Action dated Apr. 1, 2020 in Taiwanese Application No. 107113990.
Communication dated Apr. 22, 2020 from European Patent Office in EP Application No. 17889363.2.
International Preliminary Report on Patentability and Written Opinion of PCT/JP2018/016115 dated Oct. 29, 2019.
Office Action dated Jun. 26, 2020 issued in U.S. Appl. No. 16/471,692.
Michal Svozil et al., "In Vitro Studies on Transdermal Permeation of Butorphanol," Drug Development and Industrial Pharmacy, 2007, pp. 559-567 (11 pages), vol. 33.
International Search Report of PCT/JP2018/016115 dated Jun. 26, 2018.

* cited by examiner

*Primary Examiner* — Ernst V Arnold
(74) *Attorney, Agent, or Firm* — Sughrue Mion, PLLC

(57) ABSTRACT

A patch comprises a backing layer and an adhesive layer, wherein the adhesive layer contains at least one selected from the group consisting of butorphanol and pharmaceutically acceptable salts thereof, and contains a rubber-based adhesive base and a silicone-based adhesive base, and a mass ratio of the rubber-based adhesive base to the silicone-based adhesive base (the mass of the rubber-based adhesive base:the mass of silicone-based adhesive base) in the adhesive layer is 9.5:0.5 to 1.9:8.1.

4 Claims, No Drawings

PATCH

CROSS REFERENCE TO RELATED APPLICATIONS

This application is a National Stage of International Application No. PCT/JP2018/016115 filed Apr. 19, 2018, claiming priority based on Japanese Patent Application No. 2017-086357 filed Apr. 25, 2017 and Japanese Patent Application No. 2017-129601 filed Jun. 30, 2017.

TECHNICAL FIELD

The present invention relates to a patch, and more particularly relates to a patch containing butorphanol and/or a pharmaceutically acceptable salt thereof.

BACKGROUND ART

Butorphanol is a general name of 17-(cyclobutylmethyl)morphinan-3,14-diol having a molecular structure of morphinan skeleton. Butorphanol is a drug classified as an opioid analgesic and is generally used as an injectable formulation containing butorphanol tartrate which is a tartaric acid addition salt of butorphanol. Butorphanol is also disclosed as N-cyclobutylmethyl-3,14-dihydroxymorphinan, for example, in U.S. Pat. No. 3,775,414 (PLT 1).

Further, for example, M. Svozil et al., Drug Development and Industrial Pharmacy, 2007, 33(5), pp. 559-567 (NLT 1) teaches that butorphanol is used as a drug of a transdermal absorption preparation. Furthermore, International Publication No. WO2016/060122 (PLT 2) discloses a patch comprising a backing layer and an adhesive layer, the adhesive layer containing at least one selected from the group consisting of butorphanol and pharmaceutically acceptable salts thereof, and containing a higher aliphatic alcohol and an uncrosslinked polyvinylpyrrolidone containing no vinyl acetate as a constituent monomer. As an adhesive base contained in the adhesive layer of such a patch, there are known a rubber-based adhesive base, an acrylic adhesive base, a silicone-based adhesive base, a urethane-based adhesive base, and the like.

CITATION LIST

Patent Literature

[PTL 1] U.S. Pat. No. 3,775,414
[PTL 2] International Publication No. WO2016/060122

Non Patent Literature

[NPL 1] M. Svozil et al., Drug Development and Industrial Pharmacy, 2007, 33, pp. 559-567

SUMMARY OF INVENTION

Technical Problem

Some patches are required to be applied to the skin for a long period of time depending on an administration purpose of a drug, and rubber-based adhesive bases such as a styrene-isoprene-styrene block copolymer (SIS) and polyisobutylene (PIB) are mainly used from the viewpoint of having excellent adhesive strength. However, as a result of further studies on the patches containing butorphanol and/or a pharmaceutically acceptable salt thereof, the present inventors have found that use of the rubber-based adhesive base as an adhesive base resulted in insufficient adhesion to the skin in some cases and that there was a demand for superior adhesion to the skin. In particular, in the case where a patch containing an analgesic, namely, butorphanol and/or a pharmaceutically acceptable salt thereof is applied for a long period of time, the patch is required to exhibit superior skin permeability of butorphanol, and maintain sufficient adhesion to the skin even under conditions such as warm water conditions or high humidity conditions at the time of bathing, exercising, and so on. In the present invention, the adhesion of a patch is defined as a property in which the surface of the patch in contact with the skin firmly sticks to the skin and does not peel off, and the adhesive force of the adhesive layer means a force of adhesion to the skin that the adhesiveness of the adhesive base contained in the adhesive layer contributes for the total force of adhesion.

The present invention has been made in view of the above problems, and has an object to provide a patch having superior skin permeability of butorphanol and having adhesion to the skin at a high level excellent in water resistance and moisture resistance.

Solution to Problem

The present inventors have continuously conducted earnest studies to achieve the above object, and consequently have found that a patch comprising a backing layer and an adhesive layer remarkably inhibits deterioration of the adhesion due to warm water or high humidity, and exhibits particularly excellent adhesion to the skin when the adhesive layer contains at least one selected from the group consisting of butorphanol and pharmaceutically acceptable salts thereof (hereinafter referred to as "butorphanol and/or pharmaceutically acceptable salt thereof" in some cases), and contains a rubber-based adhesive base and a silicone-based adhesive base, and a blending ratio (mass ratio) of the rubber-based adhesive base and the silicone-based adhesive base is set within a specific range. Further, the present inventors have found that when the rubber-based adhesive base and the silicone-based adhesive base are combined at the specific blending ratio, the patch can maintain the sufficiently high maximum transdermal flux rate and exhibit excellent skin permeability, even though the content of the butorphanol and/or pharmaceutically acceptable salt thereof per unit area in the adhesive layer is small, and eventually have completed the present invention.

Specifically, a patch of the present invention is a patch comprising a backing layer and an adhesive layer, wherein
the adhesive layer contains at least one selected from the group consisting of butorphanol and pharmaceutically acceptable salts thereof, and contains a rubber-based adhesive base and a silicone-based adhesive base, and
a mass ratio of the rubber-based adhesive base to the silicone-based adhesive base (the mass of the rubber-based adhesive base:the mass of silicone-based adhesive base) in the adhesive layer is 9.5:0.5 to 1.9:8.1.

In the patch of the present invention, the content of the butorphanol and/or pharmaceutically acceptable salt thereof in the adhesive layer is preferably 0.2 to 2.0 mg/cm$^2$ in terms of a tartaric acid addition salt of butorphanol per unit area of the adhesive layer.

In the patch of the present invention, the content of the butorphanol and/or pharmaceutically acceptable salt thereof in the adhesive layer in terms of the tartaric acid addition salt of butorphanol is preferably 3 to 20% by mass relative to the total mass of the adhesive layer.

Furthermore, in the patch of the present invention, the content of the silicone-based adhesive base in the adhesive layer is 1 to 47% by mass relative to the total mass of the adhesive layer.

Still further, in the patch of the present invention, the adhesive layer preferably further contains at least one selected from the group consisting of tackifiers and plasticizers.

Advantageous Effects of Invention

According to the present invention, it is possible to provide a patch having superior skin permeability of butorphanol and having adhesion to the skin at a high level excellent in water resistance and moisture resistance.

DESCRIPTION OF EMBODIMENTS

Hereinafter, the present invention will be described in detail based on preferred embodiments thereof.

A patch of the present invention is a patch comprising a backing layer and an adhesive layer, wherein the adhesive layer contains at least one selected from the group consisting of butorphanol and pharmaceutically acceptable salts thereof, and contains a rubber-based adhesive base and a silicone-based adhesive base, and a mass ratio of the rubber-based adhesive base to the silicone-based adhesive base (the mass of the rubber-based adhesive base:the mass of the silicone-based adhesive base) in the adhesive layer is 9.5:0.5 to 1.9:8.1.

The patch of the present invention comprises the backing layer and the adhesive layer. As the backing layer, any backing layer publicly known as a backing layer for patches may be used as appropriate without particular limitation as long as it can support the adhesive layer to be described later. Examples of materials for the backing layer according to the present invention include: polyolefins such as polyethylene and polypropylene; an ethylene-vinyl acetate copolymer, a vinyl acetate-vinyl chloride copolymer, a polyvinyl chloride, and the like; polyamides such as nylon; polyesters such as polyethylene terephthalate (PET), polybutylene terephthalate, and polyethylene naphthalate; cellulose derivatives; synthetic resins such as polyurethane; and metals such as aluminum. Among them, the polyester and polyethylene terephthalate are preferable from the viewpoints of non-drug-adsorbing property and drug impermeability. Examples of the forms of the backing layer include: films; sheets such as sheets, porous sheets, and foamed sheets; cloths such as woven fabrics, knitted fabrics, and nonwoven fabrics; foils; and laminates thereof. Then, the thickness of the backing layer is not particular limited but is preferably within a range of 5 to 1000 μm from the viewpoints of easiness of work for applying a patch and manufacturability.

The patch of the present invention may further include a release liner on a surface of the adhesive layer opposite from the backing layer. As such a release liner, there are films, sheets, or laminates thereof which are made of materials including: polyolefins such as polyethylene and polypropylene; an ethylene-vinyl acetate copolymer, a vinyl acetate-vinyl chloride copolymer, a polyvinyl chloride, and the like; polyamides such as nylon; polyesters such as polyethylene terephthalate; cellulose derivatives; synthetic resins such as polyurethane; aluminum; paper; and so on. Preferably, in each of these release liners, the surface to be in contact with the adhesive layer is release-treated by a silicone-containing compound coating, a fluorine-containing compound coating, or the like so that the release liner can be easily peeled off from the adhesive layer.

<Drug>

The adhesive layer according to the present invention contains, as a drug, at least one selected from the group consisting of butorphanol and pharmaceutically acceptable salts thereof. In the present invention, butorphanol is defined as 17-(cyclobutylmethyl)morphinan-3,14-diol, which is expressed by a molecular formula of $C_{21}H_{29}NO_2$.

In the present invention, the form of butorphanol contained in the adhesive layer may be a free form, a pharmaceutically acceptable salt thereof, or a free form obtained by desalting a pharmaceutically acceptable salt of butorphanol during manufacturing and/or in the formulation manufactured, or may be one of them or a mixture of two or more of them. The pharmaceutically acceptable salt of butorphanol is preferably an acid addition salt from the viewpoint that the stability of the drug tends to further improve. Examples of the acid in the acid addition salt include hydrochloric acid, sulfuric acid, nitric acid, phosphoric acid, phosphorous acid, hydrobromic acid, maleic acid, malic acid, ascorbic acid, tartaric acid, lauric acid, stearic acid, palmitic acid, oleic acid, myristic acid, lauryl sulfuric acid, linolenic acid, and fumaric acid. Among them, a tartaric acid addition salt (butorphanol tartrate) expressed by the following structural formula (1) is preferred as the pharmaceutically acceptable salt of butorphanol.

[Chem. 1]

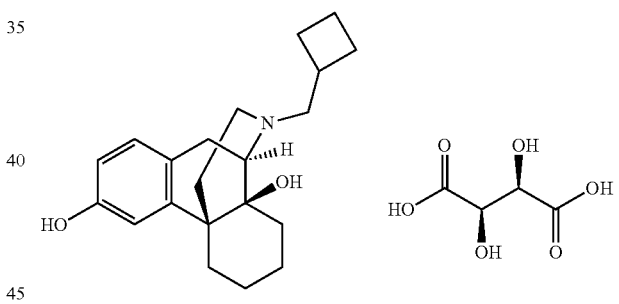

(1)

In the present invention, the content of butorphanol and/or a pharmaceutically acceptable salt thereof contained in the adhesive layer (the content of the butorphanol, the content of the pharmaceutically acceptable salt of butorphanol, or the total content of the butorphanol and the salt if both of them are contained. The same applies below) in terms of the tartaric acid addition salt of butorphanol is preferably 3 to 20% by mass, more preferably 3 to 15% by mass, even more preferably 3 to 12% by mass, and particularly preferably 3 to 10% by mass relative to the total mass of the adhesive layer. If the content of the butorphanol and/or the pharmaceutically acceptable salt thereof is less than the aforementioned lower limit, the skin permeability of butorphanol tends to decrease. On the other hand, if the content exceeds the aforementioned upper limit, crystals of butorphanol tend to precipitate and the adhesive force or the cohesive force of the adhesive layer tends to decrease.

In the present invention, when the content of the butorphanol and/or the pharmaceutically acceptable salt thereof contained in the adhesive layer is specified as the content in terms of the tartaric acid addition salt of butorphanol per unit area of the adhesive layer, the content is preferably 0.2 to 2.0 mg/cm², more preferably 0.2 to 1.5 mg/cm², even more preferably 0.2 to 1.2 mg/cm², and particularly preferably 0.2 to 1.0 mg/cm². In the present invention, even though the content of the butorphanol and/or the pharmaceutically acceptable salt thereof per unit area is relatively small (for example, 0.2 to 0.9 mg/cm², 0.3 to 0.7 mg/cm², or 0.3 to 0.65 mg/cm²), the patch is capable of exhibiting superior skin permeability of butorphanol. If the content of the butorphanol and/or the pharmaceutically acceptable salt thereof per unit area is less than the aforementioned lower limit, the maximum transdermal flux rate of butorphanol tends to be small. On the other hand, if the content exceeds the aforementioned upper limit, crystals of butorphanol tend to precipitate and the adhesive force or the cohesive force of the adhesive layer tends to decrease.

The adhesive layer according to the present invention may further contain a drug other than the butorphanol and pharmaceutically acceptable salts thereof as long as the drug does not impair the effect of the present invention. Examples of drugs other than the butorphanol and pharmaceutically acceptable salts thereof include nonsteroidal antiinflammatory analgesics (such as diclofenac, indomethacin, ketoprofen, felbinac, loxoprofen, ibuprofen, flurbiprofen, tiaprofen, acemetacin, sulindac, etodolac, tolmetin, piroxicam, meloxicam, ampiroxicam, naproxen, azapropazone, methyl salicylate, glycol salicylate, valdecoxib, celecoxib, rofecoxib, and amfenac), antipyretic analgesics (such as acetaminophen), antihistamines (such as diphenhydramine, chlorpheniramine, mequitazine, and homochlorocyclodine), antihypertensive agents (such as diltiazem, nicardipine, nilvadipine, metoprolol, bisoprolol, and trandolapril), antiparkinsonian drugs (such as pergolide, ropinirole, bromocriptine, and selegiline), bronchodilators (such as tulobuterol, isopretenolol, and salbutamol), antiallergic agents (such as ketotifen, loratadine, azelastine, terfenadine, cetirizine, and acitazanorast), local anesthetics (such as lidocaine and dibucaine), neuropathic pain remedies (such as pregabalin), non-narcotic analgesics (such as buprenorphine, tramadol, and pentazocine), anesthetic analgesics (such as morphine, oxycodone, and fentanyl), drugs for organa urinaria (such as oxybutynin and tamsulosin), drugs for psychoneurosis (such as promazine and chlorpromazine), steroid hormone agents (such as estradiol, progesterone, norethisterone, cortisone, and hydrocortisone), antidepressants (such as sertraline, fluoxetine, paroxetine, and citalopram), anti-dementia drugs (such as donepezil, rivastigmine, and galantamine), antipsychotic drugs (such as risperidone and olanzapine), central nerve stimulants (such as methylphenidate), drugs for osteoporosis treatment (such as raloxifene and alendronate), prophylactic drugs for breast cancer (such as tamoxifen), anti-obesity drugs (such as mazindole and dibutramine), insomnia remedies (such as melatonin), and anti-rheumatic drugs (such as actarit). One of these drugs may be used alone, or two or more of them may be used in combination. When the other drugs are contained in the adhesive layer, the total content of the other drugs is preferably 50% by mass or less relative to the total mass of the adhesive layer.

<Adhesive Base>

The adhesive layer according to the present invention needs to contain both of a rubber-based adhesive base and a silicone-based adhesive base as adhesive bases.

As the rubber-based adhesive base, there are natural rubbers and synthetic rubbers. From the viewpoint that the adhesive layer for a patch more tends to maintain a sufficient adhesive force, the rubber-based adhesive base is more preferably at least one selected from the group consisting of synthetic rubbers not having a polar functional group (such as a hydroxyl group, a carboxyl group, and an amino group), such as a styrene-isoprene-styrene block copolymer (SIS), an isoprene rubber, polyisobutylene (PIB), a styrene-butadiene-styrene block copolymer (SBS), a styrene-butadiene rubber (SBR), and polybutene. One of these rubber-based adhesive bases may be used alone, or two or more of them may be used in combination. However, from the viewpoint that the adhesive layer for a patch more tends to maintain a sufficient adhesive force, it is particularly preferable to use any one of SIS and PIB alone, or to use a combination of SIS and PIB at a mass ratio (the mass of SIS:the mass of PIB) in a range of 9:1 to 1:9 (even more preferably in a range of 9:1 to 1:3 and particularly preferably in a range of 9:1 to 1:2).

In the present invention, the silicone-based adhesive base refers to a polymer (polysiloxane) containing siloxane units each expressed by the following structural formula (2) and having siloxane bonds (—Si—O—) as a main chain.

[Chem. 2]

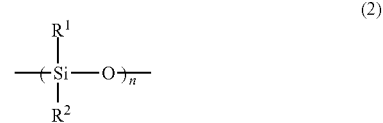

(2)

In the siloxane unit expressed by the formula (2), n represents a numerical value of 2 or more. Then, $R^1$ and $R^2$ each independently represent a group bonded to a Si atom. $R^1$ and $R^2$ are not particularly limited, but it is preferable that each of $R^1$ and $R^2$ be independently a hydrogen atom, a hydroxyl group, an alkyl group, an alkenyl group, an aryl group, or an alkoxy group. The polymer may be any of a linear polymer, a branched polymer, and a cyclic polymer, or may be a composite of them. The termini of the polymer are not particularly limited, but it is preferable that each terminus be independently a hydrogen atom, a hydroxyl group, an alkyl group, an alkenyl group, an aryl group, an alkoxy group, a trimethylsilyl group, or a trimethylsilyloxy group.

Agents usable as the silicone-based adhesive base according to the present invention include silicone rubbers referred to as MQ (polydimethylsiloxane, $R^1$ and $R^2$ in the formula (2) are methyl groups), VMQ (polymethylvinylsiloxane), PMQ (polymethylphenylsiloxane), and PVMQ (polyphenylvinylmethyl siloxane) according to the ASTM standard (ASTM D 1418); mixtures each containing at least one of the aforementioned rubbers and a silicone resin, such as polyditrimethylsilyl siloxane, other than the silicone rubber; and the like. One of them may be used alone, or two or more of them may be used in combination. When a silicone resin other than the silicone rubber is mixed, the content of the silicone resin is preferably 0.1 to 20% by mass relative to the total mass of the silicone-based adhesive base. The silicone-based adhesive base according to the present invention preferably contains at least one silicone rubber selected from the group consisting of polydimethylsiloxane, polymethylvinylsiloxane, polymethylphenylsiloxane, and polyphenylvinylmethyl siloxane. Moreover, in the silicone-based adhesive base according to the present invention, it is more preferable that the silanol groups contained in the silicone rubber be each independently capped (end-capped) with an alkyl group, an alkenyl group, an aryl group, an alkoxy group, a trimethylsilyl group, or a trimethylsilyloxy group.

In addition, commercially available agents may be used as these silicone-based adhesive bases. Examples of them are silicone adhesives provided by Dow Corning Corp. under the following product numbers: BIO-PSA7-410X, BIO-PSA7-420X, BIO-PSA7-430X, BIO-PSA7-440X, BIO-PSA7-450X, BIO-PSA7-460X (X in the preceding numbers is independently 1 or 2), BIO-PSA AC7-4201, BIO-PSA AC7-4301, BIO-PSA AC7-4302, MD7-4502, MD7-4602, 7-9700, MG7-9800, MG7-9850, BIO-PSA 7-4560 which is a hot melt silicone adhesive, and the like. One of them may be used alone or two or more of them may be used in combination.

Moreover, for the purpose of enhancing the cohesiveness of the adhesive layer, the silicone-based adhesive base according to the present invention may be modified as follows. For example, in the case where the agent has methyl groups, a peroxide is further blended for dehydrogenation, thereby crosslinking the methyl groups by removing hydrogen atoms from the methyl groups. In the case where the agent has vinyl groups, the vinyl groups are crosslinked by bonding a crosslinking agent composed of a siloxane compound containing SiH groups. In the case where the agent has hydroxyl groups (in other words, has silanol groups), the silanol groups are crosslinked by dehydrative condensation.

In the present invention, the mass ratio of the rubber-based adhesive base to the silicone-based adhesive base contained in the adhesive layer (the mass of the rubber-based adhesive base:the mass of the silicone-based adhesive base) needs to be 9.5:0.5 to 1.9:8.1. In addition, the mass ratio is more preferably 9.0:1.0 to 1.9:8.1, even more preferably 8.0:2.0 to 1.9:8.1, further more preferably 7.6:2.4 to 1.9:8.1, and particularly preferably 5.0:5.0 to 2.5:7.5. The content of the silicone-based adhesive base relative to the rubber-based adhesive base is less than the aforementioned lower limit, the adhesion of the adhesive layer to the skin, in particular, the adhesion under the warm water conditions or high humidity conditions tends to decrease. On the other hand, the content exceeds the aforementioned upper limit, the adhesion of the adhesive layer to the skin tends to decrease under any conditions other than the above specified conditions, and it tends to be difficult to uniformly mix the rubber-based adhesive base and the silicone-based adhesive base during manufacturing.

In the present invention, the content of the rubber-based adhesive base contained in the adhesive layer is preferably 5 to 50% by mass and more preferably 7 to 40% by mass relative to the total mass of the adhesive layer. If the content of the rubber-based adhesive base is less than the aforementioned lower limit, the adhesion of the adhesive layer to the skin tends to decrease. In addition, it tends to be difficult to uniformly mix the rubber-based adhesive base and the silicone-based adhesive base during manufacturing. On the other hand, if the content exceeds the aforementioned upper limit, the content of the silicone-based adhesive base decreases relative to the content of the rubber-based adhesive base. In this case, the adhesion of the adhesive layer to the skin, in particular, the adhesion under the warm water conditions or the high humidity conditions tends to decrease.

Moreover, in the present invention, the content of the silicone-based adhesive base contained in the adhesive layer is preferably 1 to 47% by mass, more preferably 1 to 45% by mass, and even more preferably 1 to 38% by mass relative to the total mass of the adhesive layer. If the content of the silicone-based adhesive base is less than the aforementioned lower limit, the adhesion of the adhesive layer to the skin, in particular, the adhesion under the warm water conditions or the high humidity conditions tends to decrease. On the other hand, if the content exceeds the aforementioned upper limit, the content of the rubber-based adhesive base decreases relative to the content of the silicone-based adhesive base. In this case, the adhesive force of the adhesive layer tends to decrease, and it tends to be difficult to uniformly mix the rubber-based adhesive base and the silicone-based adhesive base during manufacturing.

In addition, the adhesive layer according to the present invention may further contain an adhesive base other than the rubber-based adhesive base and the silicone-based adhesive base as long as the other adhesive base does not impair the effect of the present invention. An example of the adhesive base other than the rubber-based adhesive base and the silicone-based adhesive base is an acrylic adhesive base. More specifically, there are acrylic adhesive bases, listed as adhesive agents in "Pharmaceutical Excipients Directory 2016 (Japanese Version) (edited by International Pharmaceutical Excipients Council Japan)", such as a copolymer of acrylic acid/octyl acrylate, a copolymer of 2-ethylhexyl acrylate/vinyl pyrrolidine, a copolymer of acrylic ester/vinyl acetate, a copolymer of 2-ethylhexyl acrylate/2-ethylhexyl methacrylate/dodecyl methacrylate, a copolymer resin of methyl acrylate/2-ethylhexyl acrylate, a copolymer of 2-ethylhexyl acrylate/methyl acrylate/acrylic acid/glycidyl methacrylate, a copolymer of 2-ethylhexyl acrylate/vinyl acetate/hydroxyethyl acrylate/glycidyl methacrylate, a copolymer of 2-ethylhexyl acrylate/diacetone acrylamide/acetoacetoxyethyl methacrylate/methyl methacrylate, a copolymer of ethyl acrylate/methyl methacrylate, an acrylic polymer contained in an acrylic resin alkanolamine solution. One of them may be used alone or two or more of them may be used in combination. In the case where the other adhesive base as listed above is contained in the adhesive layer, the content thereof is preferably 60% by mass or less relative to the total mass of the adhesive layer.

<Absorption Enhancer>

The adhesive layer according to the present invention may further contain an absorption enhancer (transdermal absorption enhancer) as long as the absorption enhancer does not impair the effect of the present invention. An example of the absorption enhancer is at least one selected from the group consisting of aliphatic alcohols, fatty acid esters, fatty acid amides, and aliphatic alcohol ethers. Among them, preferred is at least one selected from the group consisting of aliphatic alcohols and fatty acid esters from the viewpoint that the maximum transdermal flux rate of butorphanol (Jmax) tends to be particularly high.

(Aliphatic Alcohol)

The aliphatic alcohol according to the present invention is preferably a monovalent aliphatic alcohol having 6 to 20 carbon atoms. If the number of carbon atoms in the aliphatic alcohol is less than the aforementioned lower limit, the skin irritation tends to be strong. On the other hand, if the number exceeds the aforementioned upper limit, a waxy agglomerate may be formed in the formulation. Examples of the aliphatic alcohols having 6 to 20 carbon atoms include lauryl alcohol, myristyl alcohol, cetyl alcohol, stearyl alcohol, isostearyl alcohol, oleyl alcohol, linolenyl alcohol, octyldodecanol, and mixtures thereof. Among them, a particularly preferable one is one selected from the group consisting of isostearyl alcohol, oleyl alcohol, and octyldodecanol from the viewpoint that the skin permeability of butorphanol tends to further improve.

(Fatty Acid Ester)

The fatty acid ester according to the present invention is preferably one selected from the group consisting of alkyl esters of fatty acids having 6 to 20 carbon atoms (fatty acid alkyl esters), esters of fatty acids having 6 to 20 carbon atoms with glycerol or polyglycerol (glycerol fatty acid esters), esters of fatty acids having 6 to 20 carbon atoms with polyoxyalkylene (polyoxyalkylene fatty acid esters), and esters of fatty acids having 6 to 20 carbon atoms with saccharides (fatty acid esters of saccharides).

In the present invention, the fatty acid alkyl ester is an ester compound of a fatty acid having 6 to 20 carbon atoms with a lower alkyl alcohol. Examples of such fatty acid alkyl esters include isopropyl myristate, oleyl oleate, isopropyl palmitate, triethyl citrate, ethyl linoleate, hexyl laurate, cetyl myristate, octyl dodecyl myristate, decyl oleate, otyldodecyl oleate, octyldodecyl neodecanoate, cetyl ethylhexanoate, cetyl palmitate, stearyl stearate, and mixtures of them. Among them, preferred is at least one selected from the group consisting of isopropyl myristate and isopropyl palmitate from the viewpoint that the skin permeability of butorphanol tends to further improve.

In the present invention, examples of the glycerol fatty acid esters include glycerol monolaurate (monolaurin), polyglycerol monolaurate, glycerol monostearate (monostearin), polyglycerol monostearate, glycerol monooleate (monoolein), polyglycerol monooleate, glyceryl trimyristate, glyceryl tri(caprylic-capric acid), glyceryl triisostearate, and glyceryl trioctanoate. It is preferable that the polymerization degree in the polyglycerol be 50 or less. Among them, a preferable glycerol fatty acid ester is at least one selected from the group consisting of glycerol monolaurate, polyglycerol monolaurate, glycerol monostearate, polyglycerol monostearate, glycerol monooleate, and polyglycerol monooleate.

Further, the glycerol fatty acid ester may be one in which a polyoxyethylene (POE) group is further added to an OH group in the glycerol. The degree of oxyethylene polymerization in the polyoxyethylene group is preferably 50 or less.

In the present invention, the polyoxyalkylene fatty acid ester is a compound in which a polyoxyalkylene such as ethylene glycol, polyethylene glycol, propylene glycol, polypropylene glycol, or a copolymer compound of oxyethylene and oxypropylene is ester-bonded to a portion of a carboxy group in a fatty acid having 6 to 20 carbon atoms. Such fatty acid esters with polyoxyalkylene include ethylene glycol monolaurate, polyoxyethylene monolaurate (hereinafter, polyoxyethylene is abbreviated to "POE" and oxyethylene is abbreviated to "OE" in some cases), propylene glycol monolaurate (PGML), polyoxypropylene monolaurate (hereinafter, polyoxypropylene is abbreviated to "POP" and oxypropylene is abbreviated to "OP" in some cases), ethylene glycol monopalmitate, POE monopalmitate, propylene glycol monopalmitate, POP monopalmitate, ethylene glycol monostearate, POE monostearate, propylene glycol monostearate, POP monostearate, ethylene glycol monooleate, POE monooleate, propylene glycol monooleate, POP monooleate, dioleate propylene glycol, and polyethylene glycol distearate. It is preferable that the degree of polymerization in each of the copolymers with POE, POP, OE, and OP be independently 50 or less. Among them, a particularly preferable polyoxyalkylene fatty acid ester is propylene glycol monolaurate from the viewpoint that the maximum transdermal flux rate of butorphanol (Jmax) tends to be particularly high.

In the present invention, the fatty acid ester of saccharide is a compound in which a saccharide is ester-bonded to a portion of a carboxy group of a fatty acid having 6 to 20 carbon atoms. As the saccharides, there are tetrasaccharides (erythrose and threose), penta-saccharides (xylose and arabinose), hexa-saccharides (glucose and galactose), sugar alcohols (xylitol and sorbitol), disaccharides (sucrose, lactose, and maltose), and the like. Fatty acid esters with such saccharides include sorbitan monolaurate (Span 20), sorbitan monopalmitate (Span 40), sorbitan monostearate (Span 60), sorbitan tristearate (Span 65), sorbitan monooleate (Span 80), sorbitan trioleate, and sorbitan sesquioleate (Span 83).

In addition, the fatty acid ester with the saccharide may be one in which a polyoxyethylene (POE) group is further added to an OH group in a sugar residue. The degree of oxyethylene polymerization in the polyoxyethylene group is preferably 50 or less. Such compounds are polysorbate 20 (Tween 20), polysorbate 40 (Tween 40), polysorbate 60 (Tween 60), polysorbate 65 (Tween 65), polysorbate 80 (Tween 80), and the like.

(Fatty Acid Amide)

The fatty acid amide according to the present invention is an amide of a fatty acid having 6 to 20 carbon atoms. Examples thereof include lauric acid diethanolamide, oleic acid diethanolamide, stearic acid diethanolamide, ethylene bis-stearic acid amide, stearic acid monoamide, oleic acid monoamide, ethylene bis-oleic acid amide, erucic acid monoamide, and mixtures of them.

(Aliphatic Alcohol Ether)

In the present invention, the aliphatic alcohol ether is a compound in which polyoxyalkylene such as ethylene glycol, polyethylene glycol, propylene glycol, polypropylene glycol, a copolymer compound of oxyethylene and oxypropylene, glycerol, or polyglycerol is ether-bonded to a portion of an OH group in an aliphatic alcohol having 6 to 20 carbon atoms. Examples of such aliphatic alcohol ethers include POE oleyl ether, POE lauryl ether, POE cetyl ether, POE stearyl ether, POE octyl dodecyl ether, POE palmityl ether, and mixtures of them.

Other examples of the absorption enhancers which may be contained in the adhesive layer according to the present invention include POE hydrogenated castor oils, lecithins, phospholipids, soybean oil derivatives, triacetins, and so on.

Moreover, in the adhesive layer according to the present invention, it is also preferable that the absorption enhancer be a surface-activating compound that functions as a surfactant. Among the above-listed compounds, a preferable surface-activating compound is, for example, at least one selected from the group consisting of propylene glycol monolaurate, sorbitan monooleate, glycerol monolaurate, glycerol monooleate, polysorbate 20, polysorbate 40, polysorbate 60, and polysorbate 80. Moreover, the surface-activating compound is preferably non-ionic.

In the present invention, in the case where such an absorption enhancer is further contained in the adhesive layer, the preferable content is such that the mass ratio of the butorphanol and/or pharmaceutically acceptable salt thereof to the absorption enhancer (the mass of butorphanol and/or a pharmaceutically acceptable salt thereof in terms of a tartaric acid addition salt:the mass of the absorption enhancer) is preferably 20:1 to 1:10, and more preferably 15:1 to 1:7. In this case, the content of the absorption enhancer relative to the total mass of the adhesive layer is preferably 1 to 30% by mass and more preferably 1 to 20% by mass. If the content of the absorption enhancer is within the aforementioned range, the transdermal flux rate of butorphanol tends to achieve further enhancement.

<Additive>

The adhesive layer according to the present invention may further contain additives such as adsorbents, tackifiers, plasticizers, solubilizing agents for drugs, fillers, stabilizers, preservatives, and so on as long as the additives do not impair the effect of the present invention.

(Adsorbent)

As the adsorbents, there are inorganic and/or organic substances having hygroscopicity. More specifically, there are mineral substances such as talc, kaolin, and bentonite; silicon compounds such as fumed silica (such as Aerosil (registered trademark)) and hydrated silica; metallic compounds such as zinc oxide and dried aluminum hydroxide gel; weak acids such as lactic acid and acetic acid; sugars such as dextrin; and high molecular weight polymers such as polyvinylpyrrolidone, aminoalkyl methacrylate copolymer, crospovidone, carboxyvinyl polymer, and butyl methacrylate methyl methacrylate copolymer. One of them may be used alone, or two or more of them may be used in combination. Among them, the adhesive layer according to the present invention preferably further contains polyvinylpyrrolidone (PVP) from the viewpoint that precipitation of crystals originated from the butorphanol can be inhibited.

In the case where an adsorbent (preferably polyvinylpyrrolidone) is further contained in the adhesive layer, the content of the adsorbent is preferably 0.05 to 2 $mg/cm^2$ in terms of the content per unit area of the adhesive layer or is 1 to 20% by mass in terms of the content relative to the total mass of the adhesive layer. Further, the mass ratio of the butorphanol and/or pharmaceutically acceptable salt thereof to the polyvinylpyrrolidone (the mass of the butorphanol and/or a pharmaceutically acceptable salt thereof in terms of the tartaric acid addition salt:the mass of the polyvinylpyrrolidone) is preferably 20:1 to 1:10. If the content of the polyvinylpyrrolidone is less than the aforementioned lower limit, precipitation of crystals originated from the butorphanol tends to occur. On the other hand, if the content exceeds the aforementioned upper limit, the skin permeability of butorphanol tends to decrease and the adhesive force of the adhesive layer tends to decrease.

(Desalting Agent)

The desalting agent is blended mainly for the purpose of converting all or part of a basic drug into a free form. Such a desalting agent is not particularly limited. For example, in the case of preparing a formulation containing butorphanol in free form by blending an acid addition salt of butorphanol as the drug, the desalting agent is preferably a basic substance, and more preferably a metal ion-containing desalting agent or a basic nitrogen atom-containing desalting agent. As the metal ion-containing desalting agent, there are sodium acetate (including anhydrous sodium acetate), sodium hydroxide, potassium hydroxide, magnesium hydroxide, sodium bicarbonate, potassium bicarbonate, sodium citrate, sodium lactate, and the like. One of them may be used alone, or two or more of them may be used in combination. Among them, sodium acetate and sodium hydroxide are particularly preferable as the desalting agent. Here, the adhesive layer according to the present invention may further contain a compound derived from the basic drug and the desalting agent (for example, in the case where butorphanol tartrate and sodium acetate are mixed together, the adhesive layer may further contain sodium tartrate). In the case where the desalting agent and the compound derived from the basic drug and the desalting agent are further contained in the adhesive layer, the content in terms of the desalting agent is preferably 0.5 to 5 acid-base equivalents and more preferably 0.5 to 4 acid-base equivalents with respect to 1 acid-base equivalent of the butorphanol in terms of the tartaric acid addition salt from the viewpoint that the degradation of the drug is inhibited.

(Tackifier)

The tackifier is blended mainly for the purpose of enhancing the tackiness of the adhesive base. As such tackifiers, there are, for example, rosin-based resins, terpene-based resins, petroleum-based resins, phenol-based resins, and xylene-based resins. One of them may be used alone, or two or more of them may be used in combination. In the case where such a tackifier is further contained in the adhesive layer, the content thereof is preferably 0.5 to 50% by mass and more preferably 3 to 40% by mass relative to the total mass of the adhesive layer from the viewpoints of improvement in the adhesive force of the adhesive layer and/or relaxation of local irritation at peeling-off.

(Plasticizer)

The plasticizer is blended mainly for the purpose of adjusting properties such as the adhesive property of the adhesive layer, the flowability of the adhesive layer during manufacturing, and the transdermal absorbability of the drug. Examples of such a plasticizer include silicone oil; petroleum-based oils such as paraffin-based process oils, naphthene-based process oils, and aromatic process oils; squalane and squalene; plant oils such as olive oil, camellia oil, castor oil, tall oil, and peanut oil; dibasic acid esters such as dibutyl phthalate and dioctyl phthalate; liquid rubbers such as polybutene and liquid isoprene rubber; diethylene glycol, polyethylene glycol, propylene glycol, and dipropylene glycol; and the like. One of them may be used alone, or two or more of them may be used in combination. Among them, the silicone oil, the liquid paraffin, and the liquid polybutene are preferable as the plasticizer. In the case where such a plasticizer is further contained in the adhesive layer, the content thereof is preferably 0.5 to 25% by mass and more preferably 3 to 20% by mass relative to the total mass of the adhesive layer from the viewpoints of improvement in the adhesive force of the adhesive layer and/or relaxation of local irritation at peeling-off.

(Solubilizing Agent)

The solubilizing agent is blended mainly for the purpose of promoting dissolution of the drug. Examples of such a solubilizing agent include organic acids such as acetic acid, aliphatic alcohols, and surfactants. One of them may be used alone, or two or more of them may be used in combination. Among them, the organic acids and the aliphatic alcohols are preferable as the solubilizing agent.

(Filler)

The filler is blended mainly for the purpose of adjusting the adhesive force of the adhesive layer. Example of such a filler include aluminum hydroxide, calcium carbonate, magnesium carbonate; silicates such as aluminum silicate and magnesium silicate; silicic acid, barium sulfate, calcium sulfate, calcium zincate, zinc oxide, and titanium oxide. One of them may be used alone or two or more of them may be used in combination.

In the case where the aforementioned additives are further contained in the adhesive layer, the content in total is preferably 70% by mass or less relative to the total mass of the adhesive layer.

The total mass of the adhesive layer according to the present invention per unit area (the area of an attachment surface) is preferably 25 to 250 $g/m^2$ and more preferably 40 to 150 $g/m^2$. Then, in the present invention, even though the mass per unit area is relatively small (for example, 40 to 110 $g/m^2$ or more preferably 50 to 105 $g/m^2$), the patch can exhibit superior skin permeability of butorphanol. If the mass per unit area is less than the aforementioned lower limit, there are tendencies to decrease the skin permeability of butorphanol, decrease the adhesive force of the adhesive layer, and make it difficult to control the thickness of the adhesive layer during manufacturing. On the other hand, if the mass per unit area exceeds the aforementioned upper limit, there are tendencies to excessively increase the skin permeability of butorphanol for a patch intended to be attached for a long term, and make it difficult to control the thickness of the adhesive layer during manufacturing.

Moreover, the area of the attachment surface of the adhesive layer according to the present invention may be adjusted as appropriate depending on a treatment purpose or an application target, and is usually within a range of 0.5 to 200 $cm^2$.

The patch of the present invention may be manufactured by using any publicly-known patch manufacturing method as appropriate without any particular limitation. For example, first, butorphanol and/or a pharmaceutically acceptable salt thereof, the rubber-based adhesive base, and the silicone-based adhesive base together with the absorption enhancer, a solvent, the additives, and so on as needed are kneaded according to a generally known method to obtain a uniform adhesive layer composition. As the solvent, absolute ethanol, toluene, heptane, methanol, or the like may be used. Subsequently, this adhesive layer composition is applied onto the surface of the backing layer (usually the surface on one side) so as to have a desired mass per unit area, followed drying and removing the solvent, if necessary by heating, thereby forming the adhesive layer. Further, the resultant backing/adhesive layer is cut into pieces in a desired shape as needed to obtain the patch of the present invention.

The method for manufacturing the patch of the present invention may further comprise a step of sticking the release liner onto the surface of the adhesive layer opposite from the backing layer. In this case, the method may comprise: first applying the adhesive layer composition in a desired mass per unit area to the surface of one side of the release liner to form the adhesive layer; thereafter sticking the backing layer onto the surface of the adhesive layer opposite from the release liner; and cutting the resultant into pieces in a desired shape as needed to obtain the patch of the present invention. Then, the obtained patch may be hermetically sealed as needed in a storage package (for example, an aluminum laminate bag), thereby forming a packaged formulation.

EXAMPLES

Hereinafter, the present invention will be described more specifically based on Examples and Comparative Examples; however, the present invention is not limited to the following Examples. Here, Examples and Comparative Examples were examined in evaluation tests of water resistance and moisture resistance of adhesion and a skin permeation test in the following methods.

<Evaluation Tests of Water Resistance and Moisture Resistance of Adhesion>

Patches obtained in Examples and Comparative Examples were each cut in a size of 10 mm×500 mm, and six test samples were prepared for each of Examples and Comparative Examples by attaching the patches to phenolic resin test plates after removing the release liners. First, all the six test samples were observed to confirm the state where the entire surface of the adhesive layer of each patch completely adhered to the surface of the test plate, and the patch including its edges could not be easily peeled off.

(1) Evaluation Test of Water Resistance of Adhesion

In the evaluation test of water resistance of the adhesion assuming the conditions at a time of bathing or the like, three of the above six test samples were immersed in a constant temperature bath at 40° C. for 15 minutes. The test samples after the immersion were each evaluated according to the following criteria by checking the adhesion state of the adhesive layer of the patch to the surface of the test plate:

a: The entire surface of the adhesive layer completely tightly adhered to the surface of the test plate, and any change in the adhesion including the edges of the adhesive layer was not observed as compared with the state before the test;

b: The adhesive layer tightly adhered to the surface of the test plate, but a decrease in the adhesion at part of the edges of the adhesive layer was observed as compared with the state before the test; and c: The adhesive layer adhered to the surface of the test plate, but a decrease in the adhesion in the entire surface of the adhesive layer was observed as compared with the state before the test and the patch was easily peeled off from the test plate.

(2) Evaluation Test of Moisture Resistance of Adhesion

In the evaluation test of moisture resistance of the adhesion assuming the conditions at a time of bathing or the like, the remaining three of the above six test samples were left in a thermo-hygrostat at 40° C. and a humidity of 75% RH overnight (for about 15 hours). Each of the test samples after being left was evaluated according to the above criteria by checking the adhesion state of the adhesive layer of the patch to the surface of the test plate.

<Skin Permeation Test (In Vitro Hair-Less Mouse Skin Permeation Test)>

First, the skin of the hairless mouse body was peeled off and the fat was removed from the skin. The patch was cut in a size of 2.5 $cm^2$ and was applied to the epidermis side of the skin after the release liner was removed from the patch. This was set in a flow-through Franz cell for permeation test with the dermis side being in contact with a receptor solution, and the cell was filled with the receptor solution (PBS). Subsequently, the receptor solution was delivered at a flow rate of about 2.5 ml/hr while circulating warmed circulation water around the outer periphery so that the receptor solution was kept at 32° C., and the receptor solution was collected every fourth hour for up to 24 hours. The concentration of butorphanol in the collected receptor solution (in terms of tartaric acid) was measured by high performance liquid chromatography and an hourly amount of butorphanol permeated through the skin per unit area of the adhesive layer (in terms of tartaric acid, unit: $\mu g/cm^2/hr$) was calculated for each of the collection times, and the maximum value among the obtained values was regarded as the maximum transdermal flux rate (Jmax).

Example 1

First, 6.0 parts by mass of butorphanol tartrate, 2.1 parts by mass of anhydrous sodium acetate, 25.8 parts by mass of a rubber-based adhesive base 1 (SIS:PIB=1:1 (mass ratio)), 1.5 parts by mass of a silicone-based adhesive base (silicone adhesive agent, product number: BIO-PSA7-4201, manufactured by Dow Corning Corp.), 29.8 parts by mass of a tackifier, 15.8 parts by mass of a plasticizer, and 19.0 parts by mass of other ingredients (an absorption enhancer and an adsorbent) were added to an appropriate amount of a solvent (absolute ethanol and toluene), followed by mixing to obtain an adhesive layer composition. Then, the obtained adhesive layer composition was applied onto a release liner (a film made of polyethylene terephthalate and processed by release treatment), and the solvent was removed by drying, thereby forming the adhesive layer having a mass per unit area of 80 g/m². A backing layer (a film made of polyethylene terephthalate) was laminated onto the surface of the obtained adhesive layer opposite from the release liner, and thereby a patch was obtained in which the backing layer/the adhesive layer/the release liner were laminated in this order.

test of water resistance and evaluation test of moisture resistance of the adhesion. The evaluation results obtained are presented in Table 1 together with the ingredients (excluding a solvent) of each of the adhesive layer compositions in Examples 1 to 4 and Comparative Example 1 and 2. The following table also presents the mass ratio of the rubber-based adhesive base 1 to the silicone-based adhesive base (B:C) in the adhesive layer. In each of Examples 1 to 4 and Comparative Example 1, the three test samples examined in the evaluation test of water resistance of the adhesion had no difference in the adhesion state after the immersion, and demonstrated the evaluation result presented in Table 1. In addition, the three test samples in the evaluation test of moisture resistance of the adhesion had no difference in the adhesion state after being left, and demonstrated the evaluation result presented in Table 1.

TABLE 1

| | Comp. Ex. 1 | Ex. 1 | Ex. 2 | Ex. 3 | Ex. 4 | Comp. Ex. 2 |
|---|---|---|---|---|---|---|
| Adhesive layer composition [parts by mass] | | | | | | |
| Butorphanol tartrate (A) | 6.0 | 6.0 | 6.0 | 6.0 | 6.0 | 6.0 |
| Rubber-based adhesive base 1 (B) | 26.3 | 25.8 | 18.4 | 13.2 | 10.5 | 7.9 |
| Silicone-based adhesive base (C) | — | 1.5 | 21.9 | 36.5 | 43.8 | 51.1 |
| Anhydrous sodium acetate | 2.1 | 2.1 | 2.1 | 2.1 | 2.1 | 2.1 |
| Tackifier | 30.4 | 29.8 | 21.3 | 15.2 | 12.2 | 9.1 |
| Plasticizer | 16.2 | 15.8 | 11.3 | 8.0 | 6.4 | 4.8 |
| Others | 19.0 | 19.0 | 19.0 | 19.0 | 19.0 | 19.0 |
| Total | 100 | 100 | 100 | 100 | 100 | 100 |
| B:C [mass ratio] | 100:0 | 9.5:0.5 | 4.6:5.4 | 2.7:7.3 | 1.9:8.1 | 1.3:8.7 |
| Water resistance and moisture resistance evaluation | | | | | | |
| Immersion in water bath (40° c.) for 15 min | c | b | a | a | a | — |
| Leaving at humidity of 75% RH (40° c.) overnight | c | b | a | a | a | — |

Examples 2 to 4 and Comparative Example 1

Each patch was obtained in the same way as in Example 1 except that the ingredients presented below in Table 1 were used as the ingredients of the adhesive layer composition.

Comparative Example 2

The patch was tried to be obtained in the same way as in Example 1 except that the ingredients presented below in Table 1 were used as the ingredients of the adhesive layer composition, but the usable adhesive layer failed to be formed because the adhesive layer composition was dissociated due to poor compatibility between the rubber-based adhesive base 1 and the silicone-based adhesive base.

The patches obtained in Examples 1 to 4 and Comparative Example 1 were examined in the aforementioned evaluation

Examples 5 to 10 and Comparative Example 3

Each patch was obtained in the same way as in Example 1 except that the ingredients presented below in Table 2 were used as the ingredients of the adhesive layer composition and the mass of the adhesive layer per unit area (adhesive layer mass) was adjusted to the mass presented below in Table 2.

The patches obtained in Examples 5 to 10 and Comparative Example 3 were examined in the aforementioned skin permeation test. The obtained results are presented in Table 2 together with the ingredients (excluding a solvent) in the adhesive layer composition. The following table also presents the mass ratio of the rubber-based adhesive base 1 to the silicone-based adhesive base (B:C) in the adhesive layer and the content of butorphanol and/or a pharmaceutically acceptable salt thereof per unit area in terms of tartaric acid (Content of A).

TABLE 2

| | Comp. Ex. 3 | Ex. 5 | Ex. 6 | Ex. 7 | Ex. 8 | Ex. 9 | Ex. 10 |
|---|---|---|---|---|---|---|---|
| Adhesive layer composition [parts by mass] | | | | | | | |
| Butorphanol tartrate (A) | 6.0 | 6.0 | 6.0 | 6.0 | 6.0 | 6.0 | 6.0 |
| Rubber-based adhesive base 1 (B) | 27.4 | 19.2 | 24.6 | 24.6 | 24.6 | 24.6 | 24.6 |
| Silicone-based adhesive base (C) | — | 22.8 | 7.6 | 7.6 | 7.6 | 7.6 | 7.6 |
| Anhydrous sodium acetate | 2.1 | 2.1 | 2.1 | 2.1 | 2.1 | 2.1 | 2.1 |

TABLE 2-continued

|  | Comp. Ex. 3 | Ex. 5 | Ex. 6 | Ex. 7 | Ex. 8 | Ex. 9 | Ex. 10 |
|---|---|---|---|---|---|---|---|
| Tackifier | 31.6 | 22.1 | 28.5 | 28.5 | 28.5 | 28.5 | 28.5 |
| Plasticizer | 16.9 | 11.8 | 15.2 | 15.2 | 15.2 | 15.2 | 15.2 |
| Others | 16.0 | 16.0 | 16.0 | 16.0 | 16.0 | 16.0 | 16.0 |
| Total | 100 | 100 | 100 | 100 | 100 | 100 | 100 |
| B:C [mass ratio] | 10:0 | 4.6:5.4 | 7.6:2.4 | 7.6:2.4 | 7.6:2.4 | 7.6:2.4 | 7.6:2.4 |
| Adhesive layer mass[g/m$^2$] | 113 | 104 | 101 | 89 | 82 | 62 | 52 |
| Content of A per unit area[mg/cm$^2$] | 0.68 | 0.62 | 0.61 | 0.54 | 0.49 | 0.37 | 0.31 |
| Skin permeability | | | | | | | |
| Maximum transdermal flux rate (Jmax) [μg/cm$^2$/hr] | 14.7 | 21.5 | 19.4 | 15.7 | 18.8 | 17.8 | 17.1 |

Examples 11 to 14

Each patch was obtained in the same way as in Example 1 except that the ingredients presented below in Table 3 were used as the ingredients of the adhesive layer composition. In Table 3, a rubber-based adhesive base 2 refers to a rubber-based adhesive base in which the blending mass ratio of SIS to PIB (SIS:PIB) is 7:3.

The patches obtained in Examples 11 to 14 were examined in the aforementioned evaluation test of water resistance and evaluation test of moisture resistance of the adhesion. The evaluation results obtained were presented in Table 3 together with the ingredients (excluding a solvent) of each of the adhesive layer compositions in Examples 11 to 14. The following table also presents the mass ratio of the rubber-based adhesive base 1 or 2 to the silicone-based adhesive base (B:C) in the adhesive layer. In each of Examples 11 to 14, the three test samples examined in the evaluation test of water resistance of the adhesion had no difference in the adhesion state after the immersion, and demonstrated the evaluation result presented in Table 3. In addition, the three test samples in the evaluation test of moisture resistance of the adhesion had no difference in the adhesion state after being left, and demonstrated the evaluation result presented in Table 3.

Moreover, test samples were prepared from the patches obtained in each of Examples 11 to 14 in the same way as in the aforementioned evaluation tests of water resistance and moisture resistance of the adhesion. The test samples were applied to test plates and allowed to stand for 30 minutes. Thereafter, each of the patches was peeled off from the test plate at a speed of 300 mm/min. Then, the state of the adhesive layer remaining on the surface of the test plate was observed and evaluated according to the following criteria:
a: It was observed that the adhesive layer did not remain at any part including its edges;
b: It was observed that the adhesive layer remained at part of the edges of the adhesive layer; and
c: It was observed that the adhesive layer remained at the entire surface of the adhesive layer.
The evaluation results in Example 11 and Example 14 were a, and the evaluation results in Examples 12 and 13 were b.

TABLE 3

|  | Ex. 11 | Ex. 12 | Ex. 13 | Ex. 14 |
|---|---|---|---|---|
| Adhesive layer composition [parts by mass] | | | | |
| Butorphanol tartrate(A) | 3.0 | 12.0 | 15.0 | 6.0 |
| Rubber-based adhesive base 1(B) | 25.0 | 21.1 | 19.8 | — |
| Rubber-based adhesive base 2(B) | — | — | — | 23.7 |
| Silicone-based adhesive base(C) | 7.7 | 6.5 | 6.1 | 7.3 |
| Anhydrous sodium acetate | 1.0 | 4.1 | 5.2 | 2.1 |
| Tackifier | 28.9 | 24.3 | 22.8 | 27.4 |
| Plasticizer | 15.4 | 13.0 | 12.1 | 14.5 |
| Others | 19.0 | 19.0 | 19.0 | 19.0 |
| Total | 100 | 100 | 100 | 100 |
| B:C [mass ratio] | 7.6:2.4 | 7.6:2.4 | 7.6:2.4 | 7.6:2.4 |
| Water resistance and moisture resistance evaluation | | | | |
| Immersion in water bath (40° c.) for 15 min | a | a | a | a |
| Leaving at humidity of 75% RH (40° c.) overnight | a | a | a | a |

As is apparent from the results presented in Tables 1 to 3, the patches of the present invention were observed having superior water resistance and moisture resistance of the adhesion, and sufficiently maintaining the good adhesion even under the warm water conditions or the high humidity conditions at a time of bathing or the like. Thus, the patches of the present invention can be said to have adhesion to the skin at a high level excellent in water resistance and moisture resistance. Meanwhile, it was also observed that even slight differences in the content of the silicone-based adhesive base from those of the patches of the present invention (in particular, Comparative Examples 1 and 2) resulted in a decrease in the water resistance and the moisture resistance of the adhesion and a difficulty in forming the adhesive layer. Moreover, the patches of the present invention were also observed having a sufficiently high maximum transdermal flux rate (Jmax) and exhibiting superior skin permeability even when the mass of the adhesive layer per unit area was reduced, in other words, the content of the butorphanol and/or pharmaceutically acceptable salt thereof per unit area was reduced.

INDUSTRIAL APPLICABILITY

According to the present invention, it is possible to provide a patch having superior skin permeability of butorphanol and having adhesion to the skin at a high level excellent in water resistance and moisture resistance as described above.

The invention claimed is:

1. A patch comprising a backing layer and an adhesive layer, wherein
the adhesive layer contains at least one selected from the group consisting of butorphanol and pharmaceutically acceptable salts thereof, and contains a rubber-based adhesive base and a silicone-based adhesive base,
a mass ratio of the rubber-based adhesive base to the silicone-based adhesive base in the adhesive layer is 8.0:2.0 to 1.9:8.1, and
the content of the silicone-based adhesive base in the adhesive layer is 1 to 47% by mass relative to the total mass of the adhesive layer.

2. The patch according to claim 1, wherein the content of the butorphanol and/or pharmaceutically acceptable salt thereof in the adhesive layer is 0.2 to 2.0 mg/cm$^2$ per unit area of the adhesive layer in terms of the mass of a tartaric acid addition salt of butorphanol.

3. The patch according to claim 1, wherein the content of the butorphanol and/or pharmaceutically acceptable salt thereof in the adhesive layer in terms of the mass of a tartaric acid addition salt of butorphanol is 3 to 20% by mass relative to the total mass of the adhesive layer.

4. The patch according to claim 1, wherein the adhesive layer further contains at least one selected from the group consisting of tackifiers and plasticizers.

* * * * *